United States Patent [19]

Hausheer et al.

[11] Patent Number: 5,597,829
[45] Date of Patent: Jan. 28, 1997

[54] LACTONE STABLE FORMULATION OF CAMPTOTHECIN AND METHODS FOR USES THEREOF

[75] Inventors: Frederick H. Hausheer, San Antonio; Kochat Haridas, Houston, both of Tex.

[73] Assignee: BioNumerik Pharmaceuticals, Inc., San Antonio, Tex.

[21] Appl. No.: 240,035

[22] Filed: May 9, 1994

[51] Int. Cl.$^6$ .................................................... A61K 31/44
[52] U.S. Cl. ............................................................ 514/283
[58] Field of Search ................................................ 514/283

[56] References Cited

U.S. PATENT DOCUMENTS

| | | | |
|---|---|---|---|
| Re. 32,518 | 10/1987 | Miyasaka et al. | 546/48 |
| 3,219,529 | 11/1965 | Nash et al. | 167/65 |
| 3,699,230 | 10/1972 | Beauchamp, Jr. et al. | 424/272 |
| 3,894,029 | 7/1975 | Winterfeldt et al. | 260/287 |
| 4,031,098 | 6/1977 | Sugasawa | 260/287 |
| 4,082,881 | 4/1978 | Chen et al. | 424/241 |
| 4,228,162 | 10/1980 | Luzzi et al. | 424/232 |
| 4,342,776 | 8/1982 | Cragoe, Jr. et al. | 424/274 |
| 4,513,138 | 4/1985 | Miyasaka et al. | 546/48 |
| 4,604,463 | 8/1986 | Miyasaka et al. | 544/125 |
| 4,774,236 | 9/1988 | Cook et al. | 514/176 |
| 4,775,759 | 10/1988 | Rice et al. | 546/44 |
| 4,820,816 | 4/1989 | Evans et al. | 540/205 |
| 4,894,456 | 1/1990 | Wall et al. | 546/41 |
| 4,914,205 | 4/1990 | Sawada et al. | 546/70 |
| 4,981,968 | 1/1991 | Wall et al. | 544/361 |
| 5,004,758 | 4/1991 | Boehm et al. | 514/283 |
| 5,049,668 | 9/1991 | Wall et al. | 540/481 |
| 5,053,512 | 10/1991 | Wani et al. | 546/41 |
| 5,106,742 | 4/1992 | Wall et al. | 435/233 |
| 5,225,404 | 7/1993 | Giovannella et al. | 514/81 |

FOREIGN PATENT DOCUMENTS

| | | | |
|---|---|---|---|
| 2087209 | 1/1993 | Canada | A61K 31/475 |
| 0074256 | 3/1983 | European Pat. Off. | C07D 491/22 |
| 0074770 | 3/1983 | European Pat. Off. | C07D 491/22 |
| 0088642 | 9/1983 | European Pat. Off. | C07D 491/22 |
| 0220601 | 5/1987 | European Pat. Off. | C07D 491/14 |

OTHER PUBLICATIONS

Potmesil, Milan, et al., *Camptothecins: From Bench Research to Hospital Wards*. Cancer Research 54:1431–1439, Mar. 1994.
*Oncology Bulletin*, pp. 4–5, Apr. 1994.

*Primary Examiner*—Jerome D. Goldberg
*Attorney, Agent, or Firm*—Fish & Richardson P.C.

[57] ABSTRACT

Camptothecin (CPT) an anticancer drug is poorly soluble in water. This invention overcomes this limitation by teaching novel pharmaceutically acceptable lactone stable CPT formulations for the direct administration of CPT to human subjects with cancer. The claimed invention also describes novel dosages, schedules, and routes of administration of the lactone stable CPT formulations to patients with various forms of cancer.

39 Claims, No Drawings

5,597,829

LACTONE STABLE FORMULATION OF CAMPTOTHECIN AND METHODS FOR USES THEREOF

BACKGROUND OF THE INVENTION

1. Field of the Invention

Camptothecin ("CPT") is a potent inhibitor of the enzyme Topoisomerase I and has demonstrated broad anticancer activity in a variety of preclinical tumor models. The lactone form of CPT is poorly soluble in water and has significant antitumor activity and hydrolysis of E-ring actone to the carboxylate form of CPT greatly increases the water solubility of molecule at the expense of significantly reducing its antitumor activity. A lactone stable form of CPT has not been administered by parenteral or oral routes in human subjects for the purpose of inhibiting the growth of cancer cells. This invention overcomes these limitations and claims novel pharmaceutically acceptable formulations of lactone stable CPT, methods of administration of lactone stable CPT, and antitumor compositions comprising solutions of lactone stable CPT. Additionally, this invention claims novel dosages, schedules of administration, and routes of administration of CPT formulations to humans with various forms of cancer.

2. Description of the Related Art

A. Introduction to DNA Topoisomerases

Several clinically important anticancer drugs kill tumor cells by affecting DNA topoisomerases. Topoisomerases are essential nuclear enzymes that function in DNA replication and tertiary structural modifications, such as overwinding, underwinding, and catenation, which normally arise during replication, transcription, and perhaps other DNA processes. Two major topoisomerases that are ubiquitous to all eukaryotic cells: (1) Topoisomerase I (topo I) which cleaves single stranded DNA; and (2) Topoisomerase II (topo II) which cleaves double stranded DNA. Topoisomerase I is involved in DNA replication; it relieves the torsional strain introduced ahead of the moving replication fork.

Topoisomerase I purified from human colon carcinoma cells or calf thymus has been shown to be inhibited by CPT. CPT, CPT-11 and an additional Topo I inhibitor, topotecan, has been in used in clinical trials to treat certain types of human cancer. For the purpose of this invention, CPT derivatives include CPT-11, 10-hydroxy 7-ethyl camptothecin (HECPT), 9-amino camptothecin, 10, 11 methylenedioxy camptothecin and topotecan. These CPT derivatives use the same mechanism to inhibit Topo I; they stabilize the covalent complex of enzyme and strand-cleaved DNA, which is an intermediate in the catalytic mechanism. These compounds have no binding affinity for either isolated DNA or topoisomerase I but do bind with measurable affinity to the enzyme-DNA complex. The stabilization of the topoisomerase I "cleavable complex" by CPT and derivatives is readily reversible.

Although CPT and the aforementioned CPT derivatives have no effect on topoisomerase II, these CPT derivatives stabilize the "cleavable complex" in a manner analogous to the way in which epipodophyllotoxin glycosides and various anthracyclines inhibit topoisomerase II.

Inhibition of topoisomerase I by CPT and derivatives induces protein-associated-DNA single-strand breaks. Virtually all of the DNA strand breaks observed in vitro cells treated with CPT are protein linked. However, an increase in unexplained protein-free breaks can be detected in L1210 cells treated with CPT. The compounds appear to produce identical DNA cleavage patterns in end-labeled linear DNA. It has not been demonstrated that CPT or CPT derivatives cleaves DNA in the absence of the topoisomerase I enzyme.

B. Activity of Camptothecin and Derivatives is Cell Cycle Specific

The activity of CPT is cell cycle specific. The greatest quantitative biochemical effect observed in cells exposed to CPT is DNA single-strand breaks that occur during the S-phase. Because the S-phase is a relatively short phase of the cell cycle, longer exposure to the drugs results in increased cell killing. Brief exposure of tumor cells to the drugs produces little or no cell killing, and quiescent cells are refractor. These results are likely due to two factors:

(1) The drugs inhibit topoisomerase I reversibly. Although they may produce potentially lethal modifications of the DNA structure during DNA replication, the breaks may be repaired after washout of the drug; and (2) Cells treated with topo I inhibitors, such as CPT tend to stay in G0 of the cell cycle until the drug is removed and the cleaved DNA is repaired. Inhibitors of these enzymes can affect many aspects of cell metabolism including replication, transcription, recombination, and chromosomal segregation.

C. Lactone Form Stabilizes Camptothecin Antitumor Activity and Reduces Water Solubility Utilizing HPLC and NMR techniques, researchers have demonstrated that CPT derivatives undergo an alkaline, pH-dependent hydrolysis of the E-ring lactone. The slow reaction kinetics allow one to assess whether both the lactone and non-lactone forms of the drug stabilizes the topoisomerase I-cleaved DNA complex. Studies indicate that only the closed lactone form of the drug helps stabilize the cleavable complex. This observation provides reasoning for the high degree of CPT activity observed in solid tumor models. Tumor cells, particularly hypoxic cells prevalent in solid neoplasms, have lower intracellular pH levels than normal cells. At pH levels below 7.0, the closed form of CPT predominates. Thus, the inventors maintain that CPT will be more effective at inhibiting topoisomerase I in an acidic environment than in cells having higher intracellular pH levels. It is the object of this invention to provide lactone stable CPT as the basis of the claimed subject matter. Lactone stable CPT is defined as CPT which is dissolved in DMI or DMA in the presence of a pharmaceutically acceptable acid. The presence of the acid stabilizes the lactone form of CPT. For the purpose of this invention lactone stable CPT and CPT are used interchangeably.

D. Camptothecin and Derivatives

In 1966, Wall and Wani isolated CPT from the plant, *Camptotheca acuminata*. In the early 1970's CPT reached Phase I and Phase II trials and was found to have antitumor activity, but it caused unpredictable myelosuppression and hemorrhagic cystitis. It is important to note that all of these studies used sodium hydroxide formulations of CPT which increased the water solubility of the molecule. Phase II studies with sodium CPT were limited because they induced unpredictable and severe myelosuppression, gastrointestinal toxicity, hemorrhagic cystitis, and alopecia. Clinical trials with sodium CPT were eventually discontinued because of unpredictable toxicities. To demonstrate the utility and novelty of the present invention it is useful to review the literature on human clinical trials conducted with sodium CPT administered parenterally.

In 1970, Gottlieb and coworkers reported on clinical studies with the sodium salt of camptothecin which were begun at the Baltimore Cancer Research Center in January 1969. In this clinical trial, CPT was administered as a rapidly running iv solution over a 5–10 minute period at a concentration of 2 mg of camptothecin sodium per milliliter of saline. Doses of CPT sodium from 0.5 to 10.0 mg/kg of actual or ideal body weight (whichever was less) were used. These investigators reported that because hemorrhagic sterile cystitis was noted in several of the early trials, patients receiving camptothecin sodium were well hydrated either i.v. or orally for 72 hours after drug administration. It is interesting to note that the mean urine recovery of CPT was 17.4% over the first 48 hours (range: 3.6–38.9%) with most of the excretion occurring in the initial 12 hours. When these investigators excluded the 5 patients with impaired excretion, the mean urine recovery of CPT was 22.8%. These investigators noted that unmetabolized camptothecin in high concentrations rapidly appeared in the urine after iv drug administration and went further to state that this finding probably accounted for the sterile hemorrhagic cystitis noted in 3 moderately dehydrated patients. Although maintaining a copious urine outflow seems able to prevent this complication, we are exploring various alterations in urine pH as another possible way of decreasing the risk of this debilitating type of toxicity.

In 1972, Muggia et. al. reported results of a Phase I clinical trial in fifteen patients treated with CPT sodium at four weekly dose levels ranging from 20–67 mg/m$^2$. No clinical benefit was observed in eight patients with measurable disease who were treated with the 5-day courses at dose levels associated with toxicity. The drug was administered in concentrations of 1 or 10 mg/ml and it was always administered by intravenous push. Cystitis was the most prominent nonhematologic toxic effect observed in this study. Bladder toxicity was dose limiting in three patients receiving doses of 20 to 30 mg/m$^2$, and occurred in two additional patients at doses of 44 and 30 mg/m$^2$. Cystitis, another toxic effect occurring frequently after treatment with camptothecin, was not predicted by preclinical toxicologic studies. Our clinical experience would suggest that the occurrence of cystitis may be related to the duration of the patient's exposure to the drug. CPT is excreted unchanged by the kidneys, although a large percentage of the drug administered cannot be accounted for in the urine. It is possible that relatively less drug is excreted in the urine of animals since an extremely active transport of CPT into bile has been demonstrated. Alternatively, one needs to postulate that the mucosa of the human bladder is more susceptible to the toxic action of CPT or that the effect on the human bladder is due to some unrecognized CPT metabolite.

In 1972, Moertel and coworkers administered CPT sodium dissolved in physiologic saline at a concentration of 2 mg/ml and administered by rapid intravenous infusion over 5–10 minutes. Two schedules of administration were used in this study: (a) a single injection repeated at 3-week intervals; and (b) a 5-day course repeated ever 4 weeks. The initial dose for the single-dose method was 180 mg/m$^2$. Because of toxic effects which were considered excessive by the investigators, later patients were treated at doses ranging between 90 and 120 mg/m$^2$. Dosages for the 5-day course ranged between 11 and 22 mg/m$^2$/day (total course: 55–110 mg/m:). The toxicity and response data from this study is summarized in Table 1–Table 4. Diarrhea was only a problem at higher doses, but then could be quite severe to the point of fecal incontinence and persistent for as long as 4 weeks. Cystitis usually began about 7–10 days after treatment and was characterized clinically by dysuria and frequency. With more severe toxicity, gross hematuria developed. Pathologically, this was characterized by multiple necrotic ulcerations which could involve the entire urinary tract from kidney pelvis to bladder. According to these investigators, the occurrence of hemorrhagic cystitis did not preclude further treatment with CPT, and its severity could be titrated down by lowering the dose in subsequent courses. These investigators also reported that the more prolonged schedule produced more severe toxicity at a given total dose level, but the difference was not as great as might have been predicted by preclinical animal studies.

These investigators proposed that a reasonable initial dose of CPT sodium is 110–120 mg/m$^2$ for the single-injection method or 17 mg/m$^2$/day (total dose: 85 mg/m$^2$) for the 5-day course. They noted that after 2 months (8 or 9 weeks) only two of their 61 patients showed evidence of partial objective improvement, and none showed improvement at 3 months. Both patients who demonstrated an objective response at 2 months had large bowel cancer. These investigators concluded that CPT "is a drug of protean and unpredictable toxicity that has no clinical value in the management of gastrointestinal cancer."

TABLE 1

Toxic Reactions: Single-Dose Method
Nonhematologic Toxicity No. of Patients With:

| Dose (mg/m$^2$) | No. of Patients Treated | Diarrhea | Cystitis |
|---|---|---|---|
| 90 | 10 | | |
| 100 | 6 | — | 2 |
| 110 | 2 | 1 | 1 |
| 120 | 7 | 4 | 2 |
| 180 | 9 | 2 | 3 |

TABLE 2

Toxic Reactions: 5-day Course
Nonhematologic No. of Patients With:

| Dose (mg/m$^2$ × 5) | No. of Patients Treated | Diarrhea | Cystitis |
|---|---|---|---|
| 11 | 2 | — | 1 |
| 15 | 9 | 1 | 4 |
| 17 | 5 | 4 | 2 |
| 20 | 10 | 4 | 6 |
| 22 | 1 | 1 | — |

TABLE 3

Relationship of Method of Administration to Cystitis

| | Method of Administration | |
|---|---|---|
| Cystitis | Single Dose (% of 34 Patients) | 5-Day Course (% of 27 Patients) |
| | 24 | 48 (P < 0.05) |

TABLE 4

Objective Results

Single-Dose Method (34 Patients)

| Objective Results* | Time after start of therapy | | | |
|---|---|---|---|---|
| | 3 wks | 6 wks | 9 wks | 12 wks |
| Improved | 4 | 2 | 2 | — |
| Stable | 17 | 11 | 8 | 6 |
| Worse | 13 | 21 | 24 | 28 |

5-Day Course (27 Patients)

| Objective results* | Time after start of therapy | | |
|---|---|---|---|
| | 4 wks | 8 wks | 12 wks |
| Improved | 1 | — | — |
| Stable | 12 | 7 | 6 |
| Worse | 14 | 20 | 21 |

*3 patients showed 25%–50% response at 3 wks only.

Gottlieb and Luce reported the results of treatment of patients with malignant melanoma with CPT sodium (1972). Fifteen patients with advanced malignant melanoma were treated with CPT at doses of 90–360 mg/m² repeated every 2 weeks. CPT sodium was administered as a single rapid intravenous (iv) injection starting at a dose of 120 mg/m² repeated at 2-week intervals. The dose in subsequent courses was increased by increments of 60 mg/m² per dose (to a maximum of 360 mg/m²) in eight patients who tolerated their initial doses with minimal toxicity. To prevent the known bladder toxicity of this drug, patients were well hydrated for 3 days after therapy. None of the patients had a 50% or greater decrease in tumor diameter. Less pronounced transient tumor regression was noted in three patients, but no clinical benefit was associated with these responses. The remaining patients had no change or progression in their disease. Toxic effects included myelosuppression (11 patients), nausea and vomiting, alopecia, diarrhea, and hemorrhagic cystitis. These investigators concluded that CPT, at least as administered in this study, had little to offer the patient with advanced disseminated melanoma.

In 1972, Creaven and co-investigators reported studies of plasma CPT levels during a 5-day course of treatment. These investigators state that the toxicity of CPT has been widely and unpredictably variable in the course of initial clinical evaluation. Severe toxic effects occurred even though patients with obvious renal disease were excluded. In this study they investigated plasma CPT levels 24 hours after the administration of sodium CPT administered on a once daily ×5 schedule to determine whether such measurements would be of value in predicting toxicity, and observed that plasma CPT levels have little relation to the dose given when the dose is in the range of 6.5–20 mg/m²/day.

In another clinical study Muggia and co-workers reported the results of a phase I trial of weekly and daily treatment with CPT. Fifteen patients were treated at four weekly dose levels ranging from 20 to 67 mg/m² of sodium CPT. Reversible leukopenia was the major dose-limiting toxic effect. Five-day loading courses were begun at total doses of 1.5 mg/m² per course because increased sensitivity to daily administration had been noted in animal studies. Leukopenia was more prolonged after daily treatment than after weekly treatment and occurred in four of six patients receiving a total dose of 100 mg/m². Tolerance to 5-day courses was an unexpected result. Also unpredicted by preclinical studies was man's susceptibility to cystitis with either schedule of treatment. They noted clinical responses in two of ten patients in whom response could be evaluated after weekly courses of treatment. No clinical benefit was observed in eight patients with measurable disease who were treated with the 5-day courses at dose levels associated with toxicity. Cystitis was another toxic effect occurring frequently after treatment with CPT, was not predicted by preclinical toxicologic studies. The investigators suggested that the occurrence of cystitis may be related to the duration of the patient's exposure to the drug, and proposed that CPT is excreted unchanged by the kidneys, although a large percentage of the drug administered cannot be accounted for in the urine. They also proposed from this study that it is possible that relatively less drug is excreted in the urine of animals since an extremely active transport of camptothecin into bile has been demonstrated. They also postulated that the mucosa of the human bladder is more susceptible to the toxic action of camptothecin or that the effect on the human bladder is due to some unrecognized CPT metabolite.

There are several features which are common in these studies with sodium CPT. First is the use of sodium CPT which made the CPT more water soluble. The hydrolysis of lactone E ring to form the carboxylate species by formulating CPT in sodium hydroxide. The antitumor activity of the carboxylate form of CPT is reduced by at least 10-fold, which partially accounts for the lack of clinical response in these studies. Second is the rapid intravenous administration of the drug. CPT is an S-phase specific drug and therefore will exert a greater antitumor effect under conditions of prolonged exposure, as in a continuous intravenous infusion. The short infusion (i.v. push or rapid i.v. infusion) times in all of these studies do not allow a long enough exposure time to the drug at suitable levels, and is further compounded by the administration of the water soluble carboxylate form of CPT. A third common feature is the notable frequency of cystitis in these studies using sodium CPT.

The novel features of the present invention include the following: (1) pharmaceutically acceptable formulations which allow the direct parenteral administration of lactone stable CPT to human subjects with cancer, (2) pharmaceutically acceptable formulations which allow the direct oral administration of lactone stable CPT to human subjects with cancer, and (3) dosages and schedules for the administration of lactone stable CPT to patients with cancer by parenteral and oral routes of administration. The methods of use for the instant invention will allow the physician to titrate the dose of lactone stable CPT which is predicted to significantly reduce the frequency of hemorrhagic cystitis relative to the administration of sodium CPT. The inventors predict that by administering the carboxylate species of CPT a higher incidence of renal toxicity is observed than would be observed if the lactone species of CPT were administered.

Inventors claim that reason previous use of sodium CPT caused hemorrhagic cystitis relates to the enhanced renal excretion of the carboxylate form of CPT which when exposed to the lower pH (~pH 5) of the distal convoluted tubule in the kidney, the carboxylate form of CPT is converted to the lactone form of CPT. The formation of the lactone form in high concentration at the distal convoluted tubule resulted in a high concentration of the lactone form of CPT being excreted into the collecting duct and into the ureters and bladder which resulted in hemorrhagic cystitis. Elimination of CPT by the renal route is enhanced by administration of the carboxylate form and is reduced by administration of the lactone form. Inventors believe that by administering CPT orally or parenterally to patients substantially in the lactone form that renal elimination of CPT will be minimal and further that the incidence of hemorrhagic cystitis will be significantly reduced in patients who receive the formulations of CPT claimed in this invention.

In addition to the previously noted toxicities and limited clinical responses to CPT, CPT has also been considered unsuitable for direct clinical use because it is poorly soluble in water. One useful purpose of this invention is to formulate CPT in a pharmaceutically acceptable manner using an organic solvent or a mixture of organic co-solvents to stabilize CPT in the lactone ring form. It is this lactone stable CPT which permits direct administration of CPT to cancer patients. An additional purpose of this invention to provide certain indications, schedules, dosages and routes of administration of lactone stable CPT for the purpose of treating cancer in humans.

The selection of suitable organic solvents for pharmaceutical dosage forms is limited to those which have a high degree of physiological safety. This invention describes administration of lactone stable CPT in a pharmaceutically acceptable multi-solvent formulation, overcomes interpatient variability and drug resistance as it relates to the prodrug CPT-11 conversion to HECPT and is useful in instances where human cancer cells, because of their altered enzymatic activity, resist metabolic conversion of CPT-11 to HECPT.

Two CPT derivatives, CPT-11 and topotecan, have less sporadic toxicities but retain significant activity of the parent compound. CPT-11 and Topotecan are currently undergoing Phase I and Phase II development in the United States. 10,11 methylene dioxycamptothecin is reportedly very active in preclinical studies, but it is also reported to be relatively insoluble in water which limits its use in the clinic (Pommier, et al. 1992).

Kunimoto and co-workers demonstrated in preclinical studies of CPT administered at similar dosages of 10–100 mg/kg intraperitoneally to CDF1 mice implanted with intraperitoneal LD1210 leukemia demonstrated superior T/C (treated/control) ratios relative to mice treated in the same manner with 7-ethyl camptothecin (ECPT) and 10-hydroxy 7-ethyl camptothecin (HECPT). Their results with CPT, ECPT and HECPT were inferior to that of CPT-11 administration under the same conditions. The inventors of the current invention believe that the lesser activity observed by Kunimoto is related to the lack of an optimized pharmacologic schedule for CPT. The instant invention takes into account the requirement for administration of the lactone stable species of CPT by a prolonged, not bolus, parenteral infusion or by the repeated oral, parenteral or topical administration of the drug in a manner which closely replicates the pharmacokinetics of a continuous parenteral infusion.

Tables 5 and 6 present data summarizing Phase I and Phase II clinical trials of CPT-11. Neutropenia and diarrhea are the major reported, dose-limiting toxicities of CPT-11.

TABLE 5

| PHASE I STUDIES CPT-11 | | | | | |
|---|---|---|---|---|---|
| Investigator | Schedule | # Pts | Dose | Toxicity | Tumor Type |
| Clavel et al | 90 min. QDx 3 Q21 days | 37 | 115 mg/m²/d (33–115) | Neutropenia* diarrhea, nausea and vomiting, alopecia | Breast (1 PR) Mesothelioma (1 PR) |
| Culine et al | 90 min. Q21 days | 59 | 150 mg/m²/wk (50–150) | Neutropenia* diarrhea* vomiting, alopecia fatigue stomatitis | esophagus (1 PR) cervix (1 PR) renal (1 PR) ovarian (1 PR) |
| Negoro et al | 30 min infusion weekly | 17 | 100 mg/m² (50–150) | Neutropenia* Diarrhea*, N/V, alopecia, liver dysfunction | NS CLC (2 PRs) |
| Ohe et al | 120 hr CI Q3 wks | 36 | 40 mg/m²/d (5–40) | Diarrhea* nausea and vomiting, thrombocytopenia, anemia, liver dysfunction | None |
| Rothenberg et al | 90 mg QWx 4 Q42 days | 32 | 180 mg/m²/wk (50–180) | Diarrhea* Neutropenia, nausea, vomiting, alopecia | Colon Ca (2 PRs) |
| Rowinsky et al | 90 min infusion Q21 day | 32 | 240 mg/m² (100–345) | Neutropenia* vomiting, diarrhea abd. pain, flushing | Colon Cancer (1 PR) Cervix Ca (1 PR) |

*Dose Limiting Toxicity

TABLE 6

CPT-11 PHASE II TRIALS

| Investigator | Tumor Type | Schedule | # Pts. | Response Rate | Reported Toxicities |
|---|---|---|---|---|---|
| Fukuoka et al | Untreated Non Small Cell Lung Cancer | 100 mg/m$^2$ weekday | 73 | (23/72) PRs 31.9% | Neutropenia, diarrhea, nausea, vomiting, anorexia, alopecia |
| Masuda et al | Refractory or Relapsed Small Cell Lung Cancer | 100 mg/m$^2$ weekly | 16 | (7/15) PRs 47% | Neutropenia, diarrhea pneumonitis (12.5) |
| Negoro et al | Small Cell Lung Cancer | 100 mg/m$^2$/weekly | 41 | 2 CRs and 7 PRs 33.3% | Neutropenia (38.6%) N/V (61.5%) diarrhea (53.8%) alopecia (40.0%) |
| Ohno et al | Leukemia/ Lymphoma | 200 mg Q3 No resp. 40 mg/m$^2$ Q0x5 34% PR 20 mg/m$^2$ bid x7 25% RR | 62 | ** | Neutropenia (91%) Thrombocytopenia Gastrointestinal (76%) |
| Shimada et al | Colon cancer | 100 mg/m$^2$/week or 150 mg/m$^2$/Q 2 wks | 17 | 6/17 (PR) 46% | Neutropenia (53%) N/V (35%) diarrhea (24%) |
| Takeuchi et al | Cervical Cancer | 100 mg/m$^2$ weekly 150 mg/m$^2$ weeks | 69 | SCR 8 PR RR of 23.6% | Neutropenia (89%) N/V (51%) Diarrhea (39.1%) Alopecia (38.1%) |

**see text

E. HECPT is the Active Metabolite of CPT-11

Preclinical data, obtained by Barilero et al. on animals and more recently on humans, suggest that HECPT is the active metabolite of CPT-11 in vivo. Several different researchers administered CPT-11 and HECPT intravenously during Phase I trials and recorded the peak plasma concentrations (CpMax) at the end of the infusions. An analysis of the published mean peak plasma concentrations indicates that approximately 1.5% to 9% of the administered CPT-11 (on a per/mg basis) is converted into HECPT. The pharmacokinetic data from 30-minute intravenous infusions show a lower percentage of conversion (~1.5%) of CPT-11 to HECPT than that observed following more prolonged infusions (~9% at 40 mg/m$^2$/dx5). The reported half life of HECPT observed in humans following the administration of CPT-11 ranges from 8.8 to 39.0 hours.

The biochemical and pharmacological relationship between CPT-11 and HECPT, as well as the role these compounds play in killing cancer cells in vivo is not completely understood. Investigators studying in vitro tumor cell lines have reported that HECPT has a 3600-fold greater inhibitory activity than CPT-11 against topoisomerase I in P388 cells and that HECPT is approximately 1000-fold more potent in generating single-strand DNA breaks in MOLT3 cells (Kawato, et al (1991)). However, Kaneda et al. report that HECPT has little anti-tumor activity compared to CPT-11 in vivo. They base their findings on studies conducted using an intermittent bolus schedule (days 1, 5, and 9) and an i.p. route of administration with an intraperitoneal P388 tumor model in mice.

Ohe et al. suggest that HECPT is a more toxic moiety of CPT-11 and could be responsible for much of the toxicity attributed to CPT-11. However, these same investigators noted a lack of correlation between HECPT pharmacokinetics and dose or CPT-11 pharmacokinetics and toxicity in human subjects. Furthermore, Ohe et al. noted a large range of interpatient variability in the AUC of CPT-11 and its metabolism to HECPT, which may result in unpredictable variability in the pharmacokinetic behavior, clinical antitumor effects, and toxicity in the individual patient. The data Ohe et al. obtained (using a 5-day, continuous intravenous infusion of CPT-11) also suggests that the conversion of CPT-11 to HECPT is a saturable process. If this is so, the clinical approach to maximizing dose intensity of the active metabolite would impose additional limitations on the effective use of CPT-11.

In preclinical studies of xenografts of human tumors in nude mice, Kawato et al. report that the sensitivity of human tumors to CPT-11 is independent of their ability to produce HECPT and that the effectiveness of CPT-11 is not related to the ability of the tumor to produce HECPT. Kawato et al. suggests that HECPT production is likely to be mediated in the plasma or interstitial compartment. Kaneda et al. observed that the plasma concentration of HECPT in mice was maintained longer after CPT-11 administration than after treatment with HECPT and suggested that clinicians should maintain plasma levels of HECPT to enhance the antitumor activity. of CPT-11. The present invention has a useful advantage of not requiring activation by an enzyme in order to form the active species (as with CPT-11) and the additional advantage of being able to directly control the interpatient variability.

One of the advantages of present invention provides clinicians with the ability to directly adjust the plasma levels of CPT to the point of therapeutic tolerance by controlling the dose and the schedule of administration. The inventors contend that this should lead to a superior ability to achieve better antitumor activity and reduce interpatient variability of the plasma levels of CPT.

The different observations made in these studies suggest that direct administration of CPT by parenteral and oral administration could provide significant clinical benefit for the treatment of cancer. However, in the past, CPT has been considered insufficiently water soluble and too toxic for clinical use. The current invention overcomes the solubility problem by providing lactone stable pharmaceutically acceptable multisolvent formulations of CPT for parenteral use and also oral CPT formulations.

SUMMARY OF THE INVENTION

This invention involves the formulation and methods of use of lactone stable CPT to treat cancer in humans. For the purposes of this invention, lactone stable CPT and CPT are used interchangeably. In the case of intravenous administration of CPT, several schedules and various dosages produce sufficient levels of lactone stable CPT to yield beneficial antitumor effects in humans. The effective levels of CPT are reasonably safe in terms of the incidence and severity of specific side effects that may occur with administration and are acceptable within standard medical practice for patients undergoing treatment for cancer. Lactone stable CPT is defined as CPT dissolved in DMI or DMA in the presence of a pharmaceutically acceptable acid.

Direct administration of lactone stable CPT is likely to offer several important clinical advantages over administration of sodium CPT and CPT-11. For example:

(1) direct administration of CPT allows the clinician to tailor the administration of the active cytoxic species (lactone stable CPT) to suit the patient's tolerance;

(2) direct administration of CPT overcomes interpatient variability which may be due to polymorphism of key enzyme(s) in the metabolism of CPT-11 to HCPT; and (3) clinicians can more consistently optimize the drug dosage and schedule to achieve the maximum tolerated dose of CPT which is likely to lead to the most beneficial clinical anti-cancer effect.

Regarding the clinical utility of lactone stable CPT for the treatment of human cancer, this invention provides the following:

(1) methods of administering lactone stable CPT to patients with cancer;

(2) solutions of lactone stable CPT;

(3) antitumor compositions comprising lactone stable CPT;

(4) stable formulations of lactone stable CPT suitable for parenteral administration;

(5) pharmacologic schedules for achieving the maximum tolerated dose with acceptable clinical toxicity observed in standard clinical practice of cancer treatment;

(6) a novel oral formulation of CPT; and (7) use of lactone stable CPT for the treatment of localized complications of cancer by direct administration via instillation into various body cavities.

CPT Dissolved in Dimethylisosorbide or Dimethylacetamide and Acid

A preferred embodiment of the claimed invention is a lactone stable camptothecin (CPT) solution comprising CPT dissolved in dimethylisosorbide (DMI) in the presence of a pharmaceutically acceptable acid or dissolved in dimethylacetamide (DMA) in the presence of a pharmaceutically acceptable acid. An additional embodiment of the claimed invention is where the pharmaceutically acceptable acid is an organic carboxylic acid and the inventors prefer citric acid. Yet another embodiment of the claimed invention is that the solution of CPT contains from about 0.1 mg to about 10.0 mg activity of camptothecin per ml of solution. This concentration would be effective for both oral and parenteral administration of the CPT.

The camptothecin (CPT) solution is prepared by dissolving the desired components in dimethylisosorbide (DMI) or dimethylacetamide (DMA). For the purpose of this invention, CPT dissolved in either DMI or DMA is lactone stable CPT. Dimethylisosorbide has been used as solvent for muscle relaxants (U.S. Pat. No. 3,699,230), tetracyclines (U.S. Pat. No. 3,219,529), aspirin (U.S. Pat. No. 4,228,162), and steroids (U.S. Pat. No. 4,082,881). DMI and DMA have very good toxicity profiles and are miscible with ethanol, propylene glycol, isopropyl myristate, water, diethyl ether, corn oil, acetone, cottonseed oil, and the like.

The present invention is prepared by dissolving the desired components in DMI or DMA and the resulting solution is then filtered and the filtrate collected. The amount of lactone stable CPT contained in the solution of this invention is not specifically restricted but may be any amount convenient for pharmaceutical purposes, and may be selected according to the dosage to be prepared. A preferred capsule filling solution contains from about 0.1 mg to about 10.0 mg of CPT activity per ml of solution.

As a preferred embodiment of the claimed invention, the lactone stable camptothecin solution is prepared by dissolving the desired components in dimethylisosorbide (DMI) or dimethylacetamide (DMA) in the presence of a pharmaceutically acceptable acid.

A pharmaceutically acceptable acid is included in the solutions of the present invention. Any pharmaceutically acceptable acid may be used; for example mineral acids such as hydrochloric acid; and organic carboxylic acids, such as tartaric, citric, succinic, fumaric, or maleic acids. An organic carboxylic acid is preferred, and citric acid is most preferred. The amount of acid used may be from about 0.005 to about 0.5 parts by weight of acid per part by weight of CPT and preferably from about 0.01 to 0.3 part by weight of acid per part by weight of CPT. Citric acid is preferably used in a proportion of from about 0.05 to about 0.1, and about 0.1 part by weight in the presence of taurocholic acid or a pharmaceutically acceptable salt thereof.

In the formulations provided by the instant invention, CPT is both soluble and maintained in its active lactone form. The non-enzymatic conversion of the pH labile E ring from the closed lactone (active) to the open carboxylate form (inactive) is reduced by formulating CPT under acidic pH conditions (<5.0). Thus, a water soluble acid is included to assure that an acidic pH value is maintained upon dilution to form the micellar solution. Examples of preferred solid water-soluble organic carboxylic acids effective in this invention include citric, gluconic, maleic, tartaric, or ascorbic acids. Other acids may be employed, but citric acid is most preferred.

An object of the present invention is to provide a solution of CPT in DMI or DMA. A concentrated solution is particularly useful as a filling solution for gelatin capsules. The solution may also be formulated for parenteral use providing a useful and practical means to dissolve the drug.

When oral dosages are to be administered in a capsule form, it is clearly superior to have a concentrated solution of CPT suitable for encapsulation within a soft or hard gelatin capsule. Concentrated solutions allow the preparation of capsules of smaller size which allows easier ingestion by the patient, and may also reduce the number of capsules to be swallowed. These factors are important in view of the generally poor condition of cancer patients.

Taurocholic acid, a bile acid, may enhance in the intestinal absorption of the drug in certain patients. The present invention takes advantage of the discovery that taurocholic acid, or a pharmaceutically acceptable salt thereof, when included with CPT in a solution dosage composition, results in improved absorption of the drug following ingestion of the composition. It is believed that this is due to the formation of a micellar solution of CPT on dilution thereof with the gastric contents.

The phenomenon of micellar solubilization of poorly water-soluble drugs mediated by bile acids, including taurocholic acid, has been previously reported with respect to glutethimide, hexestrol, griseofulvin (Bates et al.), reserpine (Malone et al.) and fatty acids and cholesterol (Westergaard et al.). The use of taurocholic acid or a pharmaceutically acceptable salt thereof in the present invention involves a pharmaceutical solution of CPT which has the unique property of providing a stable apparent solution of the drug upon dilution thereof with from 1 to 100 volumes of water. The solution is stable and free of precipitate for a period of at least two hours; sufficient time to permit administration and absorption by the patient.

It has been observed with similar solutions of etoposide, a different insoluble anticancer drug, that the bioavailability of the drug following oral administration is substantially equivalent to that achieved by intravenous administration of a solution of etoposide (U.S. Pat. No. 4,713,246). Analogous to that of etoposide, it is believed that ingestion of the present dosage form of CPT and resulting dilution thereof by the stomach contents, results in the formation of a micellar solution of CPT in the stomach which is readily absorbed by the gastrointestinal tract. Applicants do not wish to be bound, however, by any theoretical explanation of the mechanism by which the superior oral bioavailability of the present CPT formulation is achieved.

In a more preferred embodiment, CPT is solubilized in a manner suitable for clinical use by forming a sterile, non-aqueous solution of 1 part of CPT per 1 to 2 ml in a vehicle comprising dehydrated ethyl alcohol 0.1–2.0 parts by weight, benzyl alcohol 0.1–2.0 parts by weight, citric acid 0.1–0.9 parts by weight, polyethylene glycol (molecular weight 200–300) 4 to 10 parts by weight, polysorbate-80 (Tween 80) 1 to 10 parts, and dimethylisosorbide 1 to 10 parts in acidified medium with a pH of 3 to 4.

This preferred embodiment of a lactone stable CPT solution in dimethylisosorbide or dimethylacetamide is summarized in the table as follows:

| Ingredients | Parts by Weight |
| --- | --- |
| Camptothecin | 1 |
| EtOH | 0.1–2.0 |
| Benzyl Alcohol | 0.1–2.0 |
| Citric Acid | 0.1–0.5 |
| PEG 300 | 5–9 |
| Dimethylisosorbide or Dimethylacetamide | 1–10 |
| Polysorbate 80 (Tween-80) | 1–10 |

Another more preferred parenteral formulation comprises CPT formulated for dilution prior to parenteral administration made of approximately 0.1 mg to 2.0 mg of CPT per 2 ml of nonaqueous solvents including 1 to 10 parts Cremaphor EL™ (polyoxyethylated castor oil), 0.1 to 2 parts dehydrated ethyl alcohol USP, dimethylisosorbide 1 to 10 parts, and citric acid 0.1–0.9 parts to adjust the final pH to between 3 to 4.

This preferred embodiment of a CPT solution in dimethylisosorbide or DMA is as follows:

| Ingredients | Parts by Weight |
| --- | --- |
| Camptothecin | 1 |
| Cremaphor EL ™ | 1–10 |
| EtOH | 0.1–2.0 |
| Citric Acid | 0.01–0.5 |
| Dimethylisosorbide or Dimethylacetamide | 1–10 |

Dosages and Schedules for Parenteral Administration of CPT Compositions

Another embodiment of this invention is a method of administration of lactone stable CPT to a patient with cancer comprising infusing a fixed amount of CPT over a period of time and repeated at predetermined intervals. For the purpose of this invention, CPT has the following formula:

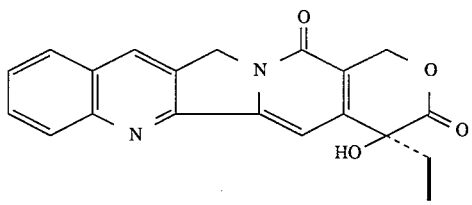

A more specific embodiment of the claimed invention is a method for administration of lactone stable CPT to a patient with cancer comprising infusing from about 2.0 mg/m$^2$ to about 33.0 mg/m$^2$ of lactone stable CPT over a duration of approximately 120 minutes every 21 to 28 days.

An additional embodiment of the claimed invention is a method for administration of CPT to a patient with cancer comprising infusing from about 1.0 mg/m$^2$ to about 16.0 mg/m$^2$ of lactone stable CPT over a duration of approximately 120 minutes for three consecutive days every 21 to 28 days.

Another embodiment of the claimed invention is a method for administration of CPT to a patient with cancer comprising infusing from about 1.0 mg/m$^2$ to about 20.0 mg/m$^2$ of lactone stable CPT over a duration of approximately 120 minutes given once per week for three consecutive weeks with 2 weeks rest after each 3 week cycle.

Another embodiment of the claimed invention is a method for administration of CPT to a previously untreated patient with cancer comprising infusing from about 2.0 mg/m$^2$ to about 24.0 mg/m$^2$ of lactone stable CPT over a duration of approximately 120 minutes given once per week for three consecutive weeks with 2 weeks rest after each 3 week cycle.

Yet another embodiment of the claimed invention is a method for administration of CPT to a patient with cancer comprising continuously infusing from about 0.1 mg/m$^2$/d to about 6.0 mg/m$^2$/d of lactone stable CPT over a duration of approximately 24 to 120 hours every 21 to 28 days.

Another embodiment of this invention when lactone stable CPT is infused into a patient with cancer, is the CPT is dissolved in dimethylisosorbide (DMI) in the presence of a pharmaceutically acceptable acid or the CPT is dissolved in dimethylacetamide (DMA) in the presence of a pharmaceutically acceptable acid.

Dosages and Schedules for Oral Administration of CPT Compositions

Another embodiment of this invention is a method of oral administration of lactone stable CPT to a patient with cancer comprising an amount of CPT given, as a single dose or divided into smaller doses, over a specified amount of time and repeated after a fixed amount of time, For the purpose of this invention, ECPT has the following formula:

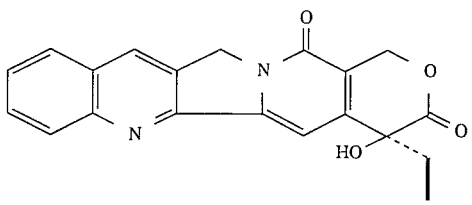

More specifically, another embodiment of this invention is a method for oral administration of lactone stable CPT to a patient with cancer comprising administering from about 2.5 mg/m$^2$ to about 100 mg/m$^2$ of lactone stable CPT in single or divided dosages within a 24 hour period every. 21 to 28 days.

Yet another embodiment of this invention is a method for oral administration of CPT to a patient with cancer comprising administering from about 1.0 mg/m$^2$ to about 50 mg/m$^2$ of lactone stable CPT daily in single or divided doses for three consecutive days every 21 to 28 days.

Another embodiment of this invention is a method for oral administration of CPT to a patient with cancer comprising administering from about 1.0 mg/m$^2$ to about 60.0 mg/m$^2$ of lactone stable CPT in single or divided dosages within a 24 hour period given once per week for three consecutive weeks with 2 weeks rest after each 3 week cycle.

Another embodiment of this invention is a method for oral administration of CPT to a previously untreated patient with cancer comprising administering from about 2.0 mg/m$^2$ to about 75 mg/m$^2$ of lactone stable CPT in single or divided doses within a 24 hour period once per week for three consecutive weeks with 2 weeks rest after each 3 week cycle.

For the purpose of this invention, a previously untreated patient is defined as a patient with cancer who has not been previously treated with any chemotherapeutic drugs.

An additional embodiment of this invention is a method for oral administration of CPT to a patient with cancer comprising administering from about 0.5 mg/m$^2$/d to about 18.0 mg/m$^2$/d of lactone stable CPT in single or divided daily doses administered within each 24 hour period for two to five consecutive days and repeated every 21 to 28 days.

Yet another embodiment of this invention for oral administration to a patient with cancer is the CPT dissolved in dimethylisosorbide (DMI) in the presence of a pharmaceutically acceptable acid or the CPT is dissolved in dimethylacetamide (DMA) in the presence of a pharmaceutically acceptable acid.

A further embodiment of this invention is the claimed composition and method of administering the composition by encapsulating the claimed formulations within a hard gelatin capsule. Yet another embodiment of the claimed composition and method of administering the composition is encapsulating the claimed formulations within a soft gelatin capsule. One of ordinary skill in the art will know that any of the claimed formulations adapted for oral administration can be used as the fill for the soft or hard gelatin capsule.

A more specific embodiment of the claimed invention is an oral formulation of lactone stable CPT in soft gelatin capsules (comprised of gelatin/glycerin/sorbitol/purifiers) containing 1.0 part of CPT in a vehicle comprising citric acid 0.1 to 0.9 parts by weight, glycerin 1 to 10 parts by weight, polyethylene glycol (molecular weight 200 to 300) 5 to 9 parts by weight, dehydrated ethyl alcohol 10 to 20% by weight of total solution weight, sodium acetate 0.05 to 0.5 parts by weight, a surfactant, and 1 to 10 parts dimethylisosorbide. A more preferred oral formulation will include as a surfactant pluronic F-127 poloxamer using 0.05 to 1.0 parts by weight.

Another preferred oral formulation will include the addition of taurocholic acid 2 to 10 parts by weight. The soft gelatin capsules may also be composed of any of a number of compounds used for this purpose including, for example, a mixture of gelatin, glycerin, sorbitol, and parabens.

The table below indicates parts by weight of different components to be included in the oral formulation to be administered in capsules. Several components are marked with an "**" which denotes that the components are "optional." For the purpose of this invention, inclusion of these components depends on a variety of different factors; i.e. type of cancer the patient has, pretreated previously, etc.

| Ingredients | Parts by Weight |
| --- | --- |
| Camptothecin | 1 |
| Citric Acid | 0.1–0.5 |
| Taurocholic Acid* | 2–10 |
| Glycerin** | 0.4–2 |
| PEG 300 | 5–9 |
| EtOH** | 10–20% by weight of total solution weight |
| Dimethylisosorbide or Dimethylacetamide | 1–10 |
| Poloxamer surfactant (Pluronic F-127)** | 0.05–1.0 |
| Sodium Acetate | 0.05–0.5 |

Clinicians will administer lactone stable CPT to human patients with cancer according to schedules that maximize its potential antitumor effects and diminish its potential toxic side effects. Except at extremely high doses which produce high plasma concentrations of the drugs, the multitumor activity of CPT-11 and CPT can be increased by increasing the duration of exposure (time dependent) rather than increasing the dose (dose dependent) of the drug. The greater antitumor effects associated with increasing the duration of exposure is a finding that is most likely related to the predominant S-phase mode of antitumor activity of CPT-11 and CPT. CPT is an S-phase-active agent; therefore, the greatest antitumor effect in humans will likely be observed with prolonged infusion or closely spaced repetitive administration schedules. Such schedules of administration would expose more cycling tumor cells to the drug and increase the frequency of exposure of the tumor cells in S-phase to sufficiently toxic levels of the drug.

Antitumor Compositions Comprising CPT

A preferred embodiment of the claimed invention is an antitumor composition comprising a solution of camptothecin dissolved in dimethylisosorbide or dimethylacetamide containing from about 0.1 mg to about 10.0 mg camptothecin activity per ml and containing from about 0.01 to about 0.9 part by weight of a pharmaceutically acceptable organic carboxylic acid per part by weight of camptothecin ("lactone stable CPT"). Inventors prefer to use 0.01 to 0.2 part by weight of a pharmaceutically acceptable organic carboxylic acid per part by weight of camptothecin.

An additional embodiment of the claimed subject matter is wherein said part by weight of a pharmaceutically organic carboxylic acid is from about 0.05 to about 0.1 part by weight per part by weight of camptothecin and the acid is citric acid.

Another embodiment of this invention is an antitumor composition comprising a solution of camptothecin dissolved in dimethylisosorbide or dimethylacetamide in the presence of a pharmaceutically acceptable acid, wherein said solution further comprises taurocholic acid or a pharmaceutically acceptable salt thereof, and polyethylene glycol.

Yet another embodiment of this invention is wherein the solution of antitumor composition contains for each part by weight of camptothecin, 1–10 parts by weight of dimethylisosorbide or dimethylacetamide, 0.005–0.5 parts by weight of a pharmaceutically acceptable acid, 1–10 parts by weight of taurocholic acid or a pharmaceutically acceptable salt thereof, and 1–10 parts by weight of polyethylene glycol. An additional embodiment is wherein said acid is an organic carboxylic acid and the inventors prefer citric acid.

Another embodiment of the claimed invention is the antitumor composition further comprises a lower alcohol. Many different alcohols would be effective in this invention, but the inventors prefer to use ethanol. Another embodiment of the claimed invention is the antitumor composition further comprises glycerin as a co-solvent.

Yet another embodiment of this invention is an antitumor composition comprising a solution of camptothecin dissolved in dimethylisosorbide or dimethylacetamide in the presence of a pharmaceutically acceptable acid, wherein said solution further comprises taurocholic acid or a pharmaceutically acceptable salt thereof, polyethylene glycol, ethanol, glycerin, and a buffer, such as sodium acetate, to maintain an acidic pH.

An additional embodiment of this invention is wherein said solution contains for each part by weight of camptothecin, 1–10 parts by weight of dimethylisosorbide or dimethylacetamide, 0.005–0.5 parts by weight of a pharmaceutically acceptable acid, 1–10 parts by weight of taurocholic acid or a pharmaceutically acceptable salt thereof, 1–10 parts by weight of polyethylene glycol, 0.1–2 parts by weight of glycerin, 0.1–2 parts by weight of ethanol, and 0.005–0.5 parts of a buffer.

Another embodiment of this invention is wherein said polyethylene glycol has a molecular weight of about 300 and the antitumor composition further comprises a non-ionic surfactant. There are many different surfactants but the inventors prefer a poloxamer. The preferred poloxamer is PF-127.

Yet another embodiment of this invention is an antitumor composition comprising a solution of camptothecin dissolved in dimethylisosorbide or dimethylacetamide in the presence of a pharmaceutically acceptable acid, wherein said solution further comprises a lower alcohol, polyethylene glycol, and surfactant.

As a more preferred embodiment for this antitumor composition, the pharmaceutically acceptable organic acid is citric acid, the polyethylene glycol has a molecular weight of about 300, the lower alcohol is ethanol and the surfactant is polysorbate-80.

Another embodiment of this invention is an antitumor composition comprising a solution of about 0.1 mg to about 10.0 mg of camptothecin dissolved in 1 to 10 parts of dimethylisosorbide or dimethylacetamide in the presence of about 0.1 to 0.5 parts of a pharmaceutically acceptable organic carboxylic acid. This antitumor composition further comprises about 5 to 9 parts by weight of polyethylene glycol, about 0.1 to 2.0 parts of a pharmaceutically acceptable alcohol, and about 1 to 10 parts of a non-ionic surfactant.

More preferred for this antitumor composition is when the acid is citric acid, the polyethylene glycol has a molecular weight of about 300, the alcohol is ethanol and the surfactant is polysorbate-80.

Another embodiment of this invention is an antitumor composition comprising a solution about 0.1 mg to about 10.0 mg of camptothecin dissolved in 1 to 10 parts of dimethylisosorbide or dimethylacetamide in the presence of 0.1 to 0.5 parts of a pharmaceutically acceptable organic carboxylic acid. This solution further comprises about 0.1 to 2.0 parts of a pharmaceutically acceptable alcohol, and about 1 to about 10 parts of a non-ionic surfactant.

More specifically for this antitumor composition, the acid is citric acid, the alcohol is ethanol, and the non-ionic surfactant is comprised of polyoxyethylated castor oil.

Another embodiment of this invention is an antitumor composition comprising a solution of 0.1 mg to about 10.0 mg of camptothecin dissolved in 1 to 10 parts of dimethylisosorbide or dimethylacetamide, wherein this solution further comprises about 1 to 10 parts polyoxyethylated castor oil, about 0.1 to 2 parts by weight dehydrated ethyl alcohol USP, and about 0.1 to 0.9 parts citric acid.

A further embodiment of this invention is that the claimed CPT composition or claimed CPT dissolved in DMI or dissolved in DMA ("lactone stable CPT") can be used in a variety of different cancer types. The claimed formulations and compositions of the invention may be used in treatment of a number of tumors including, without limitation, human cancers of the lung, breast, colon, prostate, melanoma, pancreas, stomach, liver, brain, kidney, uterus, cervix, ovaries, and urinary tract.

The site and type of tumor to be treated will, in many cases, influence the preferred route of administration and therapeutic regimen to be applied. Consequently, although the formulations of the invention may be most usually administered by intravenous injection or infusion, they also can be delivered directly into the tumor site or by other methods designed to target the drug directly to the tumor site. For example, in patients with malignant pleural effusion, the intrapleural route may be preferred; in patients with poor venous access the subcutaneous route of administration may be preferred; in patients with primary or metastatic cancer involving the brain or nervous system, the intracisternal or intrathecal route of administration may be most advantageous; in patients with malignant ascites secondary to cancer, one may select intraperitoneal administration; and in patients with bladder cancer direct intravesicular instillation may be most advantageous. Similarly, in tumors of the skin, the formulation may be topically applied. An oral formulation is also provided for use where suitable.

Thus, an additional embodiment of this invention is a lactone stable CPT solution comprising CPT dissolved in DMI or DMA, in the presence of a pharmaceutically acceptable acid and this solution is sterilized and prepared for oral, intrapleural, intrathecal, subcutaneous, intracisternal, intravesicular, intraperitoneal, topical or parenteral administration to a patient with cancer.

The formulations of the claimed invention may also be used in conjunction with other drugs in methods of convergent therapy whereupon an additional drug or drugs are co-administered along with the claimed CPT composition. Thus, lactone stable CPT may be co-administered with CPT-11, topotecan, camptothecin, or 10, 11 methylenedioxy camptothecin, using a pharmaceutically acceptable carrier, and the co-administration is based on an optimal dosage and schedule. For example, in a preferred embodiment, CPT-11 may be co-administered with CPT. Also, CPT may be co-administered with a combination of CPT-11, topotecan, camptothecin, and 10,11 methylenedioxy camptothecin, using a pharmaceutically acceptable carrier, and the co-administration is based on an optimal dosage and schedule. For example, CPT-11 and topotecan may be co-administered with the claimed CPT.

A further embodiment of claimed invention is a method of treatment of cancer in humans with convergent therapy or combination therapy. This method uses camptothecin dissolved in dimethylisosorbide (DMI) or dimethylacetamide in (DMA; "lactone stable CPT"), in the presence of pharmaceutically acceptable acid and co-administers it with additional drugs selected from the group consisting of, but not limited to, carmustine, azathioprine, cis-platinum, carboplatin, iproplatin, cyclophosphamide, ifosfamide, etoposide, ara-C, doxorubicin, daunorubicin, nitrogen mustard, 5-fluorouracil, bleomycin, mitomycin-C, fluoxymesterone, mechlorethamine, teniposide, hexamethylmelamine, leucovorin, melphelan, methotrexate, mercaptopurine, mitoxantrone, BCNU, CCNU, procarbazine, vincristine, vinblastine, vindesine, thioTEPA, amsacrine, G-CSF, GM-CSF, erythropoietin, γ-methylene-10-deazaaminopterin or γ-methylene-10-ethyl-10-deazaaminopterin, taxol, and 5-azacytidine. For the purpose of this invention, the terms convergent, co-administered, and combination are used interchangeably.

CPT in DMI or DMA when administered parenterally, is preferably diluted with an appropriate volume of a parenteral vehicle to a concentration of about 0. 1 mg/ml or lower of CPT activity. A further embodiment of the claimed invention is a sterile solution of any of the claimed CPT compositions and formulations for sterile administration to a patient with cancer upon dilution with a sterile parenteral vehicle. For the purposes of this invention, parenteral vehicles include dextrose 5 to 10% in water, 0.9%NaCl in water with or without 5% or 10% Dextrose, 0.45%NaCl in water with or without 5% or 10% Dextrose, and 3%NaCl in water with or without 5% to 10% Dextrose, or sterile lipid formulations, such as intralipid, used for parenteral nutritional support for cancer patients.

DETAILED DESCRIPTION OF PREFERRED EMBODIMENTS

In its preferred embodiments, this invention involves preparation and administration of novel lactone stable CPT formulations as described below.

EXAMPLES

The following examples illustrate selected modes for carrying out the claimed invention and are not to be construed as limiting the specification and claims in any way.

EXAMPLE 1

For injection or infusion into aqueous body fluids, a formulation comprises from about 0.1 to about 10.0 mg of CPT dissolved in 1 to 10 parts of dimethylisosorbide or dimethylacetamide in an acidified vehicle comprising between about 10 to about 40 percent of an acceptable alcohol, about 4 to about 10 parts by weight of polyether glycol, and about 1 to about 10 parts of a non-ionic surfactant. Suitable alcohols include dehydrated ethyl alcohol, benzyl alcohol. Suitable polyether glycols, include polyethylene glycol 200, polyethylene glycol 300, propylene glycol. Suitable non-ionic surfactants include polysorbate-80. In a preferred embodiment, the formulation of lactone stable CPT is supplied as an intravenous injectable in a 1 mg vial comprising a sterile, nonaqueous solution of drug in a vehicle comprising dehydrated ethyl alcohol, benzyl alcohol, citric acid, polyethylene glycol 300, and polysorbate (Tween 80) in acidified medium with a pH of 3 to 4 at a final concentration of 1 mg per 1 to 2 ml.

EXAMPLE 2

A second formulation comprises from about 0.1 mg to about 10.0 mg of CPT in an acidified vehicle comprising between about 0.1 to 2 parts of an alcohol and about 1 to 10 parts of a non-ionic surfactant. Suitable alcohols include dehydrated ethyl alcohol USP, and benzyl alcohol. Suitable non-ionic surfactants include the polyoxyethylated oils, such as polyoxyethylated vegetable oils, such as castor oil, peanut oil, and olive oil. In a preferred embodiment, 0.1 mg to 10 mg CPT is formulated in 1 to 10 parts of dimethylisosorbide or dimethylacetamide, 1 to 10 parts of Cremaphor EL™ (polyoxyethylated castor oil), 0.1 to 2 parts by weight dehydrated ethyl alcohol USP, and 0.1 to 0.9 parts citric acid to adjust the final pH between 3 to 4.

EXAMPLE 3

An oral formulation of CPT in soft gelatin capsules (comprised of gelatin/glycerin/sorbitol/purifiers/purified water) containing 1.0 part of CPT in 1 to 10 parts of dimethylisosorbide or dimethylacetamide, citric acid 0.1 to 0.5 parts by weight, purified water 1 part by weight, glycerin 1 to 10 parts by weight, and polyethylene glycol 200 to 300 5 to 9 parts by weight, dehydrated ethyl alcohol 0.2 to 2 parts by weight of total solution weight, sodium acetate 0.05 to 0.5 parts by weight, any acceptable poloxamer (i.e. pluronic F-127 poloxamer) using 0.05 to 1.0 parts by weight, and taurocholic acid 2 to 10 parts by weight. The soft gelatin capsules may also be composed of any of a number of compounds used for this purpose including, for example, a mixture of gelatin, glycerin, sorbitol, purified water, and parabens.

To prolong the stability and solubility of CPT for clinical infusions, the drug may diluted in 5% Dextrose in water (D5W) to a final concentration of 0.001 mg/ml to about 0.1 mg/ml of CPT prior to injection or infusion.

Maintaining an acidic pH (3 to 4) in the formulation is particularly important to reduce the slow conversion of CPT lactone to the E-ring-hydrolyzed carboxylate, which occurs at physiological pH. At equilibrium under physiologic pH, the ratio of the open-ring form to lactone increases. Hydrolysis of the lactone ring will be substantially reduced if the drug is kept in an acidic environment. Some of the unpredictable toxicity seen in earlier clinical trials using sodium CPT may have been due to the formation of greater amounts of the lactone form of CPT, which is 10-fold more toxic than sodium CPT in mice. The lactone form of CPT, as in CPT, is less water soluble than the carboxylate E-ring form. When early clinical trials were first conducted with CPT using NaOH, the significance of maintaining the closed lactone ring for uniform efficacy in treating patients with cancer was poorly understood. The early reported unpredictable clinical toxicities associated with CPT administration may have been exacerbated by the NaOH formulation which promotes the formation of the carboxylate form, and by the relative lack of understanding of the significance of the lactone form of CPT as it relates to antitumor activity.

The foregoing description of the formulation invention has been directed to particular preferred embodiments in accordance with the requirements of the patent statutes and for purposes of explanation and illustration. Those skilled in the art will recognize that many modifications and changes may be made without departing from the scope and the spirit of the invention.

Initially, patients may be treated in a dose escalation protocol to determine the maximal tolerated dose of the CPT formulation. In determining a safe starting dose for CPT, the data on HECPT from Tables 7 and 8 are helpful. For the purpose of this invention, "AUC" is defined as "area under the curve" and "CpMax" is defined as "the maximum plasma concentrate at the end of I.V. infusion."

not completely understood, some variability in the pharmacology and metabolic conversion of CPT-11 to HECPT probably exists based on the pharmacologic data reported from several investigators. This variability in the conversion of CPT-11 to HECPT is likely to be a result in instances of unexpected toxicity or lack of clinical effect by the use of CPT-11. In Table 8, the overall fractional concentration of the lactone species of CPT-11 and HECPT appear to remain fairly constant through a range of doses.

The administration of lactone stable CPT may be carried out using various schedules and dosages. For example:

1. For intravenous administration, a suitable dose is about 0.1 mg to about 6.0 mg/m$^2$ per day using a 3 to 5 day continuous infusion schedule every 21 to 30 days or about 2.0 to about 32.0 mg/m$^2$ given as a 30 to 90 minute infusion every 21 to 30 days.

2. Another schedule involves the administration of about 1.0 to about 16.0 mg/m$^2$ daily for three consecutive days over 90 minutes intravenously every 21 to 28 days.

TABLE 7

Analysis of AUC and CpMax Ratios of CPT-11:HECPT

|  | AUC CPT-11 (ug × hr/ml) | AUC HECPT (ug × hr/ml) | Ratio AUC CPT-11/HECPT | CpMax CPT-11:HECPT (ug/ml) | CpMax Ratio CPT 11:HECPT |
|---|---|---|---|---|---|
| Ohe et al. | | | | | |
| 25 mg/m$^2$/d × 5 | 14.1 | 1.08 | 13.0 | 1.178:0.0104 | 11.3:1 |
| 30 mg/m$^2$/d × 5 | 20.5 | 0.96 | 21.3 | 1.500:0.0105 | 14.2:1 |
| 35 mg/m$^2$/d × 5 | 20.5 | 0.91 | 22.5 | 1.538:0.0068 | 22.6:1 |
| 40 mg/m$^2$/d × 5 | 28.5 | 0.86 | 33.1 | 2.043:0.0080 | 25.5:1 |
| Rothenberg et al. | | | | | |
| 50 mg/m$^2$/wk × 4 | 1.13 | 0.0622 | 18.1 | 0.89:0.0264 | 33.7:1 |
| 100 mg/m$^2$/wk × 4 | 2.23 | 0.2148 | 10.4 | 1.29:0.0316 | 98.0:1 |
| 125 mg/m$^2$/wk × 4 | 2.97 | 0.1955 | 15.2 | 1.70:0.0393 | 43.2:1 |
| 150 mg/m$^2$/wk × 4 | 2.81 | 0.1232 | 22.8 | 1.56:0.0367 | 42.5:1 |
| 180 mg/m$^2$/wk × 4 | 3.83 | 0.2328 | 16.5 | 1.97:0.0262 | 75.2:1 |

TABLE 8

Fractional Amounts of Lactone Species of CPT-11 and HECPT as Function of Increasing Single Dose I.V. From Rothenburg et. al.

| Dose | CPT-11 AUC Based | HECPT AUC Based | CPT-11 CpMax Based | HECPT CpMax Based |
|---|---|---|---|---|
| 50 mg/m$^2$ | 0.41 | 0.29 | 0.51 | 0.50 |
| 80 mg/m$^2$ | 0.30 | 0.50 | 0.44 | 0.39 |
| 100 mg/m$^2$ | 0.33 | 0.58 | 0.53 | 0.45 |
| 125 mg/m$^2$ | 0.39 | 0.43 | 0.55 | 0.41 |
| 150 mg/m$^2$ | 0.33 | 0.30 | 0.42 | 0.36 |
| 180 mg/m$^2$ | 0.33 | 0.63 | 0.42 | 0.45 |

Data obtained using the continuous infusion schedule of Ohe et al. shows that the ratio CPT-11 to HECPT AUCs increases gradually as a function of dose and that this increase is substantially more marked in a single dose study. The data in Table 7 supports the conclusion that conversion of CPT-11 to HECPT is a saturable process which is variable among patients, and that increases in the dose (e.g., above 30 mg/m$^2$/d) of CPT-11 can result in a decrease in the CpMax of HECPT using a 5 day continuous infusion schedule. Although the factors involved in interpatient variability is 3. A suitable oral dose of the drug is about 0.5 to about 50 mg/m$^2$ per day using the lower dose for a period of 3 to 5 days and using divided dosages of administration of two to four times per day.

The parenteral and oral doses can be administered under the supervision of a physician based on gradual escalation of the dosage to achieve the maximum tolerated dose in the individual patient. The oral administration schedule of lactone stable CPT may involve multiple daily doses or single daily doses for one or more consecutive days with the ability of the physician to optimize therapy by reaching the maximum effective antitumor dose that has the least toxicity in the individual patient.

In addition, patients may be given the lactone stable CPT as an inpatient or outpatient using the following exemplary schedules:

1) about 2.0 to about 33.0 mg/m$^2$ given over 90 minutes I.V. every 21 to 28 days;

2) about 1.0 to about 16.0 mg/m$^2$ given daily for three consecutive days over 90 minutes I.V. every 21 to 28 days;

3) about 1.0 to about 20.0 mg/m$^2$ week given once per week×3 consecutive weeks over 90 minutes I.V. with 2 weeks rest after each 3 week cycle for pretreated patients;

4) about 2.0 to about 25.0 mg/m$^2$ given once per week×3 consecutive weeks over 90 minutes I.V. for previously untreated patients with 2 weeks rest after each 3 week cycle; and 5) about 0.1 to about 6.0 mg/m²/d×3 to 5 consecutive days as a continuous I.V. infusion every 21 to 28 day's.

In a preferred embodiment, lactone stable CPT is initially given at a lower dose. The dose of CPT is then escalated at each successive cycle of treatment until the patient develops side effects which demonstrates individual therapeutic tolerance. The purpose of dose escalation is to safely increases the drug levels to a maximum tolerated dose and should result in increased cytotoxicity and improved antitumor activity.

Dosages can be escalated based on patient tolerance as long as unacceptable toxicity is not observed. Since some clinical drug toxicity is anticipated in routine clinical oncology practice, appropriate treatment will be used to prevent toxicity (e.g., nausea and vomiting) or ameliorate signs and symptoms if they are observed (e.g., diarrhea). For example, antiemetics will be administered for nausea and vomiting, antidiarrheals for diarrhea, and antipyretics for fever. Appropriate dosages of steroids/antihistamines will also be used to prevent or ameliorate any anaphylactoid toxicity if an anaphylactoid reaction is observed.

Kaneda's HPLC method and further modifications by Barilero et al. are useful for the measuring quantities of CPT in plasma and tissue. In these assays, plasma, serum, and tissue homogenate samples containing CPT are immediately diluted 10-fold with 0.1N HCL to give final concentrations of about 100 ng/ml for CPT. The diluted plasma or serum samples are applied to a C18 cassette of an automated sample processor (Analytichem International, Harbor City, Calif.), which is activated with 1.5 ml of methanol and water. The HPLC apparatus (Model LC-4A; Shimadzu Seisakusho) is linked to the automated sample processor, and a C18 reversed-phase column (LiChrosorb RP-18; 25×0.4 cm; Merck) with an RP-18 precolumn is used for chromatography. The mobile phases consists of CH3CN/water (¼,v/v) for CPT. The flow rate and column temperature are 2.0 ml/min and 60 degrees Celsius for CPT. A fluoro-spectromonitor (Model RF-530; Shimadzu Seisakusho) is set at an excitation wavelength of 373 nm and an emission wavelength of 380 nm and a wavelength of 540 nm for CPT. The peak area is integrated by a data processor (Model C-RIBS Chromatopac; Shimadzu Seisakusho). CPT gives retention times of 13.8 min. Calibration curves are established for each determination by 10% mouse serum in 0.1N HCL containing CPT. Validations of CPT determinations will be made by running samples versus real standards. The limit of determination is about 1 to 5 ng for CPT using this assay.

REFERENCES

The following references may facilitate understanding or practice of certain aspects of the present invention. Inclusion of a reference in this list is not intended to and does not constitute an admission that the reference represents prior art with respect to the present invention.

| U.S. Pat. No. | | |
| --- | --- | --- |
| 3,219,529 | 11/65 | Nash, Robert A. |
| 3,699,230 | 10/72 | Beauchamp et al. |
| 4,082,881 | 04/78 | Chen, James L. |
| 4,228,162 | 10/80 | Luzzi, Louis A. |
| 4,545,880 | 10/85 | Miyasaka et al. |
| 4,473,692 | 09/84 | Miyasaka et al. |
| 4,713,246 | 1987 | Begum et al. |
| 4,778,891 | 10/88 | Tagawa et al. |
| 5,061,800 | 10/91 | Miyasaka et al. |

Other Publications

Barilero et al., Simultaneous Determination of the Camptothecin Analogue CPT-11 and Its Active Metabolite HECPT by High Performance Liquid Chromatography: Application to Plasma Pharmacokinetic Studies in Cancer Patients. J. Chromat. 575:275–280; 1992.

Bates et al., Solubilizing Properties of Bile Salt Solutions. I. Effect of Temperature and Bile Salt Concentration On Solubilization of Glutethimide, Griseofulvin and Hexostrol. Journal of Pharmaceutical Sciences, 55:191–199, (1966).

Bates et al., Rates of Dissolution of Griseofulvin and Hexestrol in Bile Salt Solutions. Chem. Abstracts 65:8680b, 1966.

Bates et al., Solubilizing Properties of Bile Salt Solutions on Glutethimide, Griseofulvin, and Hexestrol. Chem. Abstracts 64:9517e 1966; 65:15165a, 1966.

Clavel, M. et al., Phase I Study of the Camptothecin Analogue CPT-11, Administered Daily for 3 Consecutive Days. Proc. Amer. Assoc. Cancer Res. 3:83, 1992.

Creaven, P. J., Allen, L. M., Muggia, F. M. Plasma Camptothecin (NSC-100880) Levels During a 5-Day Course of Treatment: Relation to Dose and Toxicity. Cancer Chemotherapy Reports Part 1 56(5):573–578, 1972.

Culine, S., Phase I Study of the Camptothecin Analog CPT-11, Using a Weekly Schedule. Proc. of Amer. Soc. Clin. Onc. 11: 110, 1992.

Fukuoka, M. et al., A Phase H Study of CPT-11, A New Derivative of Camptothecin, for Previously Untreated Small-Cell Lung Cancer. J. Clin. Onc. 10(1):16–20, 1992.

Giovanella B. C., et al., DNA Topoisomerase I—Targeted Chemotherapy of Human Colon Cancer Xenografts. Science 246: 1046–1048; 1989.

Hsiang et al., Arrest of Replication Forks by Drug-stabilized Topoisomerase I—DNA Cleavable Complexes as a Mechanism of Cell Killing by Camptothecin Analogues. Cancer Res. 49:5077–5082, 1989.

Gottlieb, J. A., Luce, J. K. Treatment of Malignant Melanoma with Camptothecin (NSC-100880). Cancer Chemotherapy Reports Part 1 56(1): 103–105, 1972.

Jaxel, C. et al., Structure Activity Study of the Actions of Camptothecin Derivatives on Mammalian Topoisomerase I: Evidence for a Specific Receptor Site and a relation to Antitumor Activity. Cancer Res. 49:1465–1469, 1989.

Kaneda, N. et al., Metabolism and Pharmacokinetics of the Camptothecin Analogue CPT-11 in the Mouse. Cancer Research 50:1715–1720, 1990.

Kano Y, et al., Effects of CPT-11 in Combination with other Anti-Cancer Agents in Culture. Int. J. Cancer 50:604–610;1992.

Kanzawa F., et al., Role of Carboxylesterase on Metabolism of Camptothecin Analog (CPT-11) in Non-Small Cell Lung Cancer Cell Line PC-7 Cells (Meeting Abstract). Proc. Annual Meet. Am. Assoc. Cancer Res. 33:A2552; 1992.

Kawato, Y. et al., Intracellular Roles of HECPT, a Metabolite of the Camptothecin Derivative CPT-11, in the Antitumor Effect of CPT-11. Cancer Res. 51:4187–4191, 1991.

Kunimoto, T. et al., Antitumor Activity of 7-Ethyl-10-[4-(1-piperidino)-1-piperidino]Carbonyloxy-Camptothecin, a Novel Water Soluble Derivative of Camptothecin Against Murine Tumors. Cancer Res. 47:5944–5947, 1987.

Malone et al., Desoxycholic Acid Enhancement of Orally Administered Reserpine. Journal of Pharmaceutical Sciences, 55:972–974 (1966).

Masuda, N. et al., CPT-11: A New Derivative of Camptothecin for the Treatment of Refractory or Relapsed Small-Cell Lung Cancer. J. Clin. Onc. 10(8): 1225–1229 1992.

Muggia, F. M., Creaven, P. J., Hansen, H. H., Cohen, M. H., Selawry, Oleg S. Phase I Clinical Trial of Weekly and Daily Treatment with Camptothecin (NSC-100880): Correlation with Preclinical Studies. Cancer Chemotherapy Reports Part 1 56(4):515–521, 1972.

Negoro, S. et al., Phase I Study of Weekly Intravenous Infusions of CPT-11, a New Derivative of Camptothecin, in the Treatment of Advanced Non-Small Cell Lung Cancer. JNCI 83(16): 1164–1168, 1991.

Negoro, S. et al., Phase II Study of CPT-11, New Camptothecin Derivative, in Small Cell Lung Cancer. Proc. of Amer. Soc. Clin. Onc. 10:241, 1991.

Niimi S, et al., Mechanism of Cross-Resistance to a Camptothecin Analogue (CPT-11) in a Human Ovarian Cancer Cell Line Selected by Cisplatin. Cancer Res. 52:328–333; 1992.

Ohe, Y. et al., Phase I Study and Pharmacokinetics of CPT-11 with 5-Day Continuous Infusion. JNCI 84(12):972–974, 1992.

Ohno, R. et al., An Early Phase II Study of CPT-11: A New Derivative of Camptothecin, for the Treatment of Leukemia and Lymphoma. J. Clin. Onc. 8(11):1907–1912, 1990.

Pommier, Y. et al., Camptothecins: Mechanism of Action and Resistance (Meeting Abstract). Cancer Investigation, Presented at the "Chemotherapy Foundation Symposium X Innovative Cancer Chemotherapy for Tomorrow," page 3, 1992.

Rothenberg, M. L. et al., A Phase I and Pharmacokinetic Trial of CPT-11 in Patients with Refractory Solid Tumors. Amer. Soc. Clin. Onc. 11:113, 1992.

Rothenberg, M. L., Kuhn, J. G., Burris, H. A., Nelson, J., Eckardt, J. R., Tristan-Morales, M., Hilsenbeck, S. G., Weiss, G. R., Smith, L. S., Rodriguez, G. I., Rock, M. K., Von Hoff, D. D. Phase I and Pharmacokinetic Trial of Weekly CPT-11. Journal of Clinical Oncology. 11:2194–2204 (1993).

Rowinsky, E. et al., Phase I Pharmacologic Study of CPT-11, A Semisynthetic Topoisomerase I—Targeting Agent, on a Single-Dose Schedule (Meeting Abstract). Proc. of Amer. Soc. Clin. Onc. 11:115, 1992.

Sawada S. et al., Synthesis and Antitumor Activity of 20 (S)-Camptothecin Derivatives: Carbonate-Linked, Water Soluble, Derivatives of 7-Ethyl-10-hydroxycamptothecin. Chem. Pharm. Bull. 39:14446–1454; 1991.

Shimada, Y. et al., Phase II Study of CPT-11, New Camptothecin Derivative, In the Patients with Metastatic Colorectal Cancer. Proc. of Amer. Soc. Clin. Onc. 10:135, 1991.

Takeuchi, S. et al., Late Phase II Study of CPT-11, A Topoisomerase I Inhibitor, In Advanced Cervical Carcinoma (CC) (Meeting Abstract). Proc. of Amer. Soc. Clin. Onc. 11:224, 1992.

Westergaard et al., The Mechanism Whereby Bile Acid Mycelles Increase the Rate of Fatty Acid and Cholesterol Uptake Into the Intestinal Mucosal Cell. Journal of Clinical Investigation, 58: 97–108 (1976)).

The foregoing description has been directed to particular embodiments of the invention in accordance with requirements of the Patent Statutes for the purposes of illustration and explanation. It will be apparent, however, to those skilled in this art, that many modifications, changes and variations in the claimed antitumor compositions, solutions, methods of administration of the antitumor compositions set forth will be possible without departing from the scope and spirit of the claimed invention. It is intended that the following claims be interpreted to embrace all such modifications and changes.

What is claimed is:

1. A method for administration of a compound camptothecin having the formula

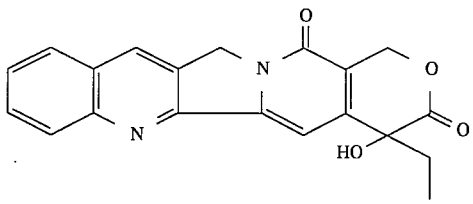

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, an effective amount of and tacurocholic acid in an admixture with an effective amount of citric acid and wherein said method of administration to a patient with cancer comprises infusing from about 2.0 mg/m$^2$ to about 33.0 mg/m$^2$ of said compound over a duration of approximately 120 minutes every 21 to 28 days.

2. A method for administration of a compound camptothecin having the formula

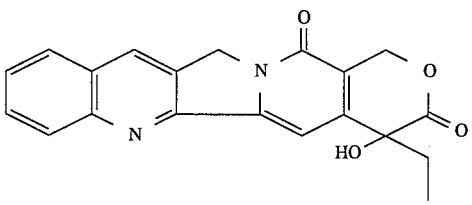

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid and wherein said method of administration to a patient with cancer comprises infusing from about 1.0 mg/m$^2$ to about 16.0 mg/m$^2$ of said compound over a duration of approximately 120 minutes for three consecutive days every 21 to 28 days.

3. A method for administration of a compound camptothecin having the formula

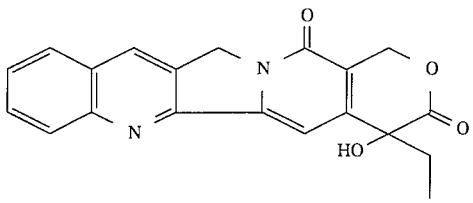

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taruocholic acid or a pharmaceutically acceptable salt thereof, and an effective amount of tacurocholic acid in an admixture with an effective amount of citric acid and wherein said method of administration to a patient with cancer comprises infusing from about 1.0 mg/m² to about 20.0 mg/m² of said compound over a duration of approximately 120 minutes given once per week for three consecutive weeks with 2 weeks rest after each 3 week cycle.

4. A method for administration of a compound camptothecin having the formula

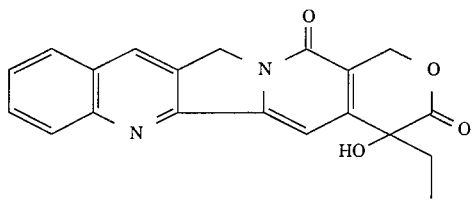

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid and wherein said method of administration to a previously untreated patient with cancer comprises infusing from about 2.0 mg/m² to about 24.0 mg/m² of said compound over a duration of approximately 120 minutes given once per week for three consecutive weeks with 2 weeks rest after each 3 week cycle.

5. A method for administration of a compound camptothecin having the formula

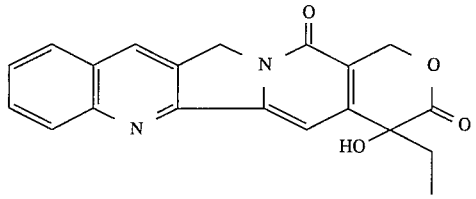

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid and wherein said method of administration to a patient with cancer comprises infusing from about 0.1 mg/m²/d to about 6.0 mg/m²/d of said compound over a duration of approximately 24 to 120 hours every 21 to 28 days.

6. A method for oral administration of a compound camptothecin having the formula

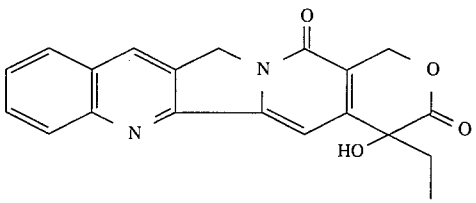

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid and wherein said method of administration to a patient with cancer comprises administering from about 2.5 mg/m² to about 100 mg/m² of said compound in single or divided dosages within a 24 hour period every 21 to 28 days.

7. A method for oral administration of a compound camptothecin having the formula

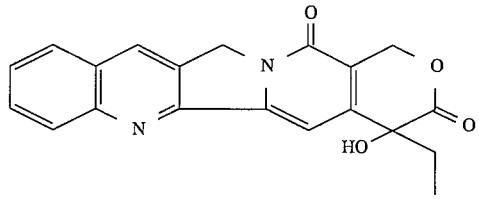

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid and wherein said method of administration to a patient with cancer comprises administering from about 1.0 mg/m² to about 50 mg/m² of said compound daily in single or divided doses for three consecutive days every 21 to 28 days.

8. A method for oral administration of a compound camptothecin having the formula

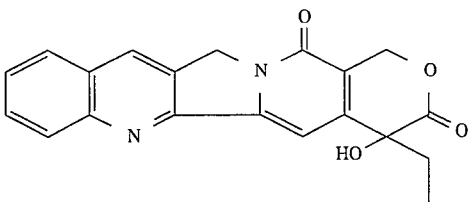

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid and wherein said method of administration to a patient with cancer comprises administering from about 1.0 mg/m$^2$ to about 60.0 mg/m$^2$ of said compound in single or divided dosages within a 24 hour period given once per week for three consecutive weeks with 2 weeks rest after each 3 week cycle.

9. A method for oral administration of a compound camptothecin having the formula

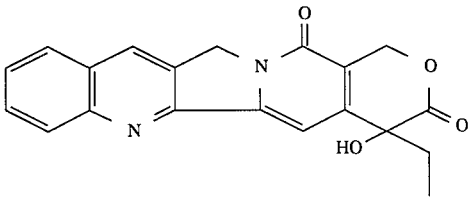

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid and wherein said method of administration to a previously untreated patient with cancer comprises administering from about 2.0 mg/m$^2$ to about 75 mg/m$^2$ of said compound in single or divided doses within a 24 hour period once per week for three consecutive weeks with 2 weeks rest after each 3 week cycle.

10. A method for oral administration of a compound camptothecin having the formula

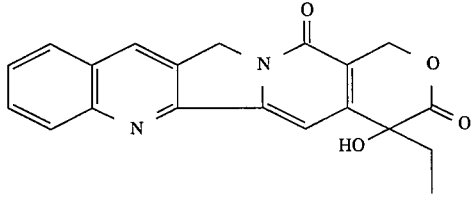

wherein said compound further comprises an effective amount of dimethylacetamide or an effective amount of dimethylisosorbide and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid and wherein said method of administration to a patient with cancer comprises administering from about 0.5 mg/m$^2$/d to about 18.0 mg/$^2$/d of said compound in single or divided daily doses administered within each 24 hour period for two to five consecutive days and repeated every 21 to 28 days.

11. A camptothecin solution comprising an effective amount of camptothecin, an effective amount of dimethylisosorbide, and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid.

12. The solution of claim 11 wherein said solution is sterilized and prepared for oral, intrapleural, intrathecal, intracisternal, intravesicular, intraperitoneal, topical or parenteral administration to a patient with cancer.

13. A camptothecin solution comprising an effective amount of camptothecin, an effective amount of dimethylacetamide, and an effective amount of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of tacurocholic acid in an admixture with an effective amount of citric acid.

14. The solution of claim 13 wherein said solution is sterilized and prepared for oral, intrapleural, intrathecal, intracisternal, intravesicular, intraperitoneal, topical or parenteral administration to a patient with cancer.

15. The solution of claim 13 wherein said acid is citric acid.

16. The solution of claims 11 or 13 said solution contains from about 0.1 mg to about 10.0 mg activity of camptothecin per ml of solution.

17. An antitumor composition comprising a solution of camptothecin, and an effective amount of dimethylisosorbide or an effective amount of dimethylacetamide containing from about 0.1 mg to about 10.0 mg camptothecin activity per ml and containing from about 0.01 to about 0.9 part by weight of a pharmaceutically acceptable acid per part by weight of camptothecin selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of taurocholic acid in an admixture with an effective amount of citric acid.

18. The antitumor composition of claim 17 wherein said acid is citric acid.

19. The antitumor composition of claim 17 wherein said parts by weight of a pharmaceutically acid is from about 0.05 to about 0.1 parts by weight per parts by weight of camptothecin.

20. An antitumor composition comprising a solution of an effective amount of camptothecin, an effective amount of dimethylisosorbide or an effective amount of dimethylacetamide, an effective amount of a pharmaceutically acceptable acid selected from the group consisting of hydrochloric acid, tartaric acid, citric acid, succinic, fumaric, maleic acid, gluconic acid, ascorbic acid, taurocholic acid and taurocholic acid, or a pharmaceutically acceptable salt thereof, wherein said solution further comprises an effective amount of taurocholic acid or a pharmaceutically acceptable salt thereof, and an effective amount of polyethylene glycol.

21. The antitumor composition of claims 20 or 30 which further comprises an effective amount of a non-ionic surfactant.

22. The antitumor composition of claim 21 wherein said surfactant is a poloxamer.

23. The antitumor composition of claim 20 wherein said solution contains for each part by weight of camptothecin, 1–10 parts by weight of dimethylisosorbide or dimethylacetamide, 0.005–0.5 parts by weight of a pharmaceutically acceptable acid, 1–10 parts by weight of taurocholic acid or a pharmaceutically acceptable salt thereof, and 1–10 parts by weight of polyethylene glycol.

24. The antitumor composition of claim 23 wherein said acid is citric acid.

25. The antitumor composition of claim 20 further comprising an effective amount of a lower alcohol.

26. The antitumor composition of claim 25 wherein said lower alcohol is an effective amount of ethanol.

27. The antitumor composition of claim 20 further comprising an effective amount of glycerin.

28. An antitumor composition comprising a solution of an effective amount of camptothecin, an effective amount of dimethylisosorbide or an effective amount of dimethylacetamide, an effective amount of a pharmaceutically acceptable acid selected from the group consisting of hydrochloric acid, tartaric acid, citric acid, succinic, fumaric, maleic acid, gluconic acid, ascorbic acid, taurocholic acid and taurocholic acid, or a pharmaceutically acceptable salt thereof, and an effective amount of taurocholic acid in an admixture with an effective amount of citric acid, an effective amount of polyethylene glycol, an effective amount of ethanol, an effective amount of glycerin, and an effective amount of a buffer.

29. The antitumor composition of claim 28 wherein said solution contains for each part by weight of camptothecin, 1–10 parts by weight of dimethylisosorbide or dimethylacetamide, 0.005–0.5 parts by weight of a pharmaceutically acceptable acid, 1–10 parts by weight of taurocholic acid or a pharmaceutically acceptable salt thereof, 1–10 parts by weight of polyethylene glycol, 0.1–2 parts by weight of glycerin, 0.1–2 parts by weight of ethanol, and 0.005–0.5 parts of a buffer.

30. The solution of claims 11, 13, 20, or 28 or wherein said solution is encapsulated within a hard gelatin capsule.

31. The solution of claims 11, 13, 20, or 28 wherein said solution is encapsulated within a soft gelatin capsule.

32. The antitumor composition of claims 20 or 28 wherein said polyethylene glycol has a molecular weight of about 300.

33. An antitumor composition comprising a solution of an effective amount of camptothecin, an effective amount of dimethylisosorbide or an effective amount of dimethylacetamide, an effective amount of a pharmaceutically acceptable acid selected from the group consisting of hydrochloric acid, tartaric acid, citric acid, succinic, fumaric, maleic acid, gluconic acid, ascorbic acid, taurocholic acid and taurocholic acid, or a pharmaceutically acceptable salt thereof, and an effective amount of taurocholic acid in an admixture with an effective amount of citric acid, an effective amount of a lower alcohol, an effective amount of polyethylene glycol, and an effective amount of surfactant.

34. The antitumor composition of claim 33 wherein said pharmaceutically acceptable acid is citric acid, wherein said polyethylene glycol has a molecular weight of about 300, wherein said lower alcohol is ethanol and wherein said surfactant is polysorbate-80.

35. An antitumor composition comprising a solution of about 0.1 mg to about 10.0 mg of camptothecin, 1 to 10 parts of dimethylisosorbide or dimethylacetamide, about 0.1 to 0.5 parts of a pharmaceutically acceptable acid selected from the group consisting of hydrochloric acid, tartaric acid, citric acid, succinic, fumaric, maleic acid, gluconic acid, ascorbic acid, taurocholic acid or a pharmaceutically acceptable salt thereof, and an effective amount of taurocholic acid in an admixture with an effective amount of citric acid, about 5 to 9 parts by weight of polyethylene glycol, about 0.1 to 2.0 parts of a pharmaceutically acceptable alcohol, and about 1 to 10 parts of a non-ionic surfactant.

36. The antitumor composition of claim 35 wherein said acid is citric acid, wherein said polyethylene glycol has a molecular weight of about 300, wherein said alcohol is ethanol and wherein said surfactant is polysorbate-80.

37. An antitumor composition comprising a solution about 0.1 mg to about 10.0 mg of camptothecin, in 1 to 10 parts of dimethylisosorbide or dimethylacetamide, 0.1 to 0.5 parts of a pharmaceutically acceptable acid selected from the group consisting of hydrochloric acid, tartaric acid, citric acid, succinic, fumaric, maleic acid, gluconic acid, ascorbic acid, and an effective amount of tacurocholic acid, or a pharmaceutically acceptable salt thereof, in an admixture with an effective amount of citric acid, about 0.1 to 2.0 parts of a pharmaceutically acceptable alcohol selected from the group consisting of ethanol (ethyl alcohol), benzyl alcohol or an admixture of ethanol (ethyl alcohol) and benzyl alcohol, and about 1 to about 10 parts of a non-ionic surfactant.

38. The antitumor composition of claim 37 wherein said acid is citric acid, wherein said alcohol is ethanol, and wherein said non-ionic surfactant is polyoxyethylated castor oil.

39. An antitumor composition comprising a solution of 0.1 mg to about 10.0 mg of camptothecin, 1 to 10 parts of dimethylisosorbide or dimethylacetamide, about 1 to 10 parts polyoxyethylated castor oil, about 0.1 to 2 parts by weight dehydrated ethyl alcohol USP, and about 0.1 to 0.9 parts citric acid.

\* \* \* \* \*